US008951244B2

(12) United States Patent
Smith

(10) Patent No.: US 8,951,244 B2
(45) Date of Patent: Feb. 10, 2015

(54) MULTI-SPOT LASER PROBE

(75) Inventor: Ronald T. Smith, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 192 days.

(21) Appl. No.: 12/946,393

(22) Filed: Nov. 15, 2010

(65) Prior Publication Data

US 2011/0144627 A1     Jun. 16, 2011

Related U.S. Application Data

(60) Provisional application No. 61/286,579, filed on Dec. 15, 2009.

(51) Int. Cl.
     *A61F 9/008*      (2006.01)

(52) U.S. Cl.
     CPC ............. *A61F 9/008* (2013.01); *A61F 9/00821* (2013.01); *A61F 9/00823* (2013.01); *A61F 2009/00863* (2013.01)
     USPC .......................................................... 606/4

(58) Field of Classification Search
     CPC .... G02B 27/106; G02B 5/1814; G02B 6/264; G02B 6/32; A61F 9/00823; A61F 9/00821; A61F 2009/00863
     See application file for complete search history.

(56) References Cited

U.S. PATENT DOCUMENTS

| | | | |
|---|---|---|---|
| 4,062,043 A | 12/1977 | Zeidler et al. | |
| 4,111,524 A | 9/1978 | Tomlinson, III | |
| 4,274,706 A | 6/1981 | Tangonan | |
| 4,679,901 A | 7/1987 | Dammann et al. | |
| 4,865,029 A * | 9/1989 | Pankratov et al. | 606/4 |
| 4,919,506 A * | 4/1990 | Covey | 385/35 |
| 4,986,262 A | 1/1991 | Saito | |
| 5,090,400 A | 2/1992 | Saito | |
| 5,125,922 A | 6/1992 | Dwyer et al. | |
| 5,150,254 A | 9/1992 | Saitou | |

(Continued)

FOREIGN PATENT DOCUMENTS

| | | |
|---|---|---|
| DE | 10 2005 055 885 | 5/2007 |
| EP | 1191359 A1 | 3/2002 |

(Continued)

OTHER PUBLICATIONS

Lang et al., "Aberration improvement of gradient index rod lens", Chinese Optics Letters, vol. 3, No. 3, Mar. 10, 2005.*

(Continued)

*Primary Examiner* — Gary Jackson
*Assistant Examiner* — Scott T. Luan
(74) *Attorney, Agent, or Firm* — Haynes and Boone, LLP

(57) ABSTRACT

A multi-spot/multi-fiber laser probe is provided that includes a first adapter; a GRIN lens within the first adapter, the GRIN lens configured to receive a laser beam from a laser source at a proximal end of the GRIN lens and to relay the received laser beam towards a distal end of the GRIN lens; and a multi-fiber array having a proximal end configured to receive the relayed laser light. In addition, a multi-spot/single-fiber laser probe is provided that includes a cannula; an optical fiber positioned within the cannula; a diffractive beam splitter within the cannula; and a GRIN lens within the cannula and arranged between a distal end of the optical fiber and the diffractive beam splitter, wherein the diffractive beam splitter is configured to split a focused laser beam from the GRIN lens into multiple diffracted laser beams.

4 Claims, 5 Drawing Sheets

(56) References Cited

U.S. PATENT DOCUMENTS

| | | |
|---|---|---|
| 5,261,904 A | 11/1993 | Baker et al. |
| 5,275,593 A | 1/1994 | Easley et al. |
| 5,356,407 A | 10/1994 | Easley et al. |
| 5,373,526 A | 12/1994 | Lam et al. |
| 5,396,571 A | 3/1995 | Saadatmanesh et al. |
| 5,409,137 A | 4/1995 | Bonomelli |
| 5,555,129 A | 9/1996 | Konno et al. |
| 5,630,809 A | 5/1997 | Connor |
| 5,659,642 A | 8/1997 | King et al. |
| 5,715,089 A | 2/1998 | Shiraishi |
| 5,738,676 A * | 4/1998 | Hammer et al. .............. 606/4 |
| 5,841,912 A | 11/1998 | Mueller-Fiedler et al. |
| 5,921,981 A | 7/1999 | Bahmanyar et al. |
| 5,973,779 A | 10/1999 | Ansari et al. |
| 5,980,454 A | 11/1999 | Broome |
| 6,066,128 A | 5/2000 | Bahmanyar et al. |
| 6,071,748 A | 6/2000 | Modlin et al. |
| 6,080,143 A | 6/2000 | Connor |
| 6,096,028 A | 8/2000 | Bahmanyar et al. |
| 6,097,025 A | 8/2000 | Modlin et al. |
| 6,241,721 B1 | 6/2001 | Cozean et al. |
| 6,370,422 B1 | 4/2002 | Richards-Kortum et al. |
| 6,421,179 B1 | 7/2002 | Gutin et al. |
| 6,441,934 B1 | 8/2002 | Boord et al. |
| 6,520,956 B1 | 2/2003 | Huang |
| 6,539,132 B2 | 3/2003 | Ivtsenkov et al. |
| 6,563,982 B1 | 5/2003 | Xie et al. |
| 6,591,042 B2 | 7/2003 | Tatah |
| 6,687,010 B1 | 2/2004 | Horii et al. |
| 6,975,898 B2 | 12/2005 | Seibel |
| 7,071,460 B2 | 7/2006 | Rush |
| 7,231,243 B2 | 6/2007 | Tearney et al. |
| 7,252,662 B2 | 8/2007 | McArdle et al. |
| 7,566,173 B2 * | 7/2009 | Auld et al. .............. 383/33 |
| 2001/0055462 A1 | 12/2001 | Seibel |
| 2002/0013572 A1 | 1/2002 | Berlin |
| 2002/0054725 A1 | 5/2002 | Ivtsenkov et al. |
| 2002/0111608 A1 | 8/2002 | Baerveldt et al. |
| 2003/0020922 A1 | 1/2003 | Crowley et al. |
| 2003/0068133 A1 * | 4/2003 | Tatah .............. 385/43 |
| 2003/0081220 A1 | 5/2003 | Ostrovsky et al. |
| 2004/0012856 A1 | 1/2004 | Gutin |
| 2004/0101247 A1 | 5/2004 | Chen et al. |
| 2004/0109164 A1 | 6/2004 | Horii et al. |
| 2004/0116909 A1 | 6/2004 | Neuberger et al. |
| 2004/0195511 A1 | 10/2004 | Elmore et al. |
| 2005/0075704 A1 | 4/2005 | Tu et al. |
| 2005/0143719 A1 * | 6/2005 | Sink .............. 606/9 |
| 2005/0154379 A1 | 7/2005 | McGowan, Sr. et al. |
| 2005/0197655 A1 | 9/2005 | Telfair et al. |
| 2005/0240168 A1 | 10/2005 | Neuberger et al. |
| 2005/0245916 A1 | 11/2005 | Connor |
| 2006/0013533 A1 | 1/2006 | Slatkine |
| 2006/0100613 A1 | 5/2006 | McArdle et al. |
| 2006/0106370 A1 | 5/2006 | Baerveldt et al. |
| 2006/0114473 A1 | 6/2006 | Tearney et al. |
| 2006/0195076 A1 | 8/2006 | Blumenkranz et al. |
| 2007/0057211 A1 | 3/2007 | Bahlman et al. |
| 2007/0121069 A1 | 5/2007 | Andersen et al. |
| 2007/0179430 A1 | 8/2007 | Smith et al. |
| 2007/0238955 A1 | 10/2007 | Tearney et al. |
| 2007/0265602 A1 | 11/2007 | Mordaunt et al. |
| 2007/0299430 A1 | 12/2007 | McArdle et al. |
| 2008/0013960 A1 | 1/2008 | Tearney et al. |
| 2008/0097225 A1 | 4/2008 | Tearney et al. |
| 2008/0308730 A1 | 12/2008 | Vizi et al. |
| 2009/0015923 A1 | 1/2009 | Auld et al. |
| 2009/0043296 A1 * | 2/2009 | Foster et al. .............. 606/11 |
| 2010/0027943 A1 * | 2/2010 | Armani et al. .............. 385/74 |
| 2013/0038836 A1 | 2/2013 | Smith |

FOREIGN PATENT DOCUMENTS

| | | |
|---|---|---|
| JP | 2000-500043 | 5/1998 |
| JP | 2008-544809 | 12/2008 |
| WO | WO 97/17011 | 5/1997 |
| WO | 99/08612 A1 | 2/1999 |
| WO | 2006/116141 A1 | 11/2006 |
| WO | WO 2007/005313 | 11/2007 |
| WO | 2009/009246 | 1/2009 |

OTHER PUBLICATIONS

Chen et al., "GRIN lens for LD beam collimation and shaping", in Advanced Optical Manufacturing and Testing Technology 2000, Li Yang, Harvey M. Pollicove, Qiming Xin, James C. Wyant, Editors, Proceedings of SPIE vol. 4231 (2000).*

European extended Search Report for corresponding European Application No. 10838081.7 dated Jul. 18, 2013, 6 pages.

Chinese Office Action with English translation issued for CN 201080056929.6 dated Dec. 31, 2013, 19 pgs.

Japanese Office Action with English translation issued for JP 2012-544531 dated Sep. 30, 2014, 19 pgs.

* cited by examiner

MULTI-SPOT LASER PROBE

This application claims priority to U.S. Provisional application Ser. No. 61/286,579 filed on Dec. 15, 2009.

TECHNICAL FIELD

This application relates to a laser probe for use in ophthalmic procedures and more particularly to a multi-spot laser probe for use in photocoagulation.

BACKGROUND

Laser photocoagulation therapy addresses ocular conditions such as retinal detachments and tears as well as proliferative retinopathy resulting from diseases such as diabetes. The abnormally high blood sugar in a diabetic stimulates the retinal vessels to release growth factors that in turn encourage an undesirable proliferation of blood vessels and capillaries over the retinal surface. These proliferated blood vessels are very delicate and will readily bleed into the vitreous. The body responds to the damaged vessels by producing scar tissue, which may then cause the retina to detach so as to eventually cause blindness.

In laser photocoagulation, a laser probe is used to cauterize the blood vessels at various laser burn spots across the retina. Because the laser will also damage the rods and cones that are present in the retina to allow vision, eyesight, as well as the blood vessels, is affected. Since vision is most acute at the central macula of the retina, the surgeon arranges the resulting laser burn spots in the peripheral areas of the retina. In this fashion, some peripheral vision is sacrificed to preserve central vision. During the procedure, the surgeon drives the probe with a non-burning aiming beam such that the retinal area to be photocoagulated is illuminated. Due to the availability of low-power red laser diodes, the aiming beam is generally a low-power red laser light. Once the surgeon has positioned the laser probe so as to illuminate a desired retinal spot, the surgeon activates the laser through a foot pedal or other means to then photocoagulate the illuminated area. Having burned a retinal spot, the surgeon repositions the probe to illuminate a new spot with the aiming light, activates the laser, repositions the probe, and so on until a suitable array of burned laser spots are distributed across the retina.

The number of required laser photocoagulations for any one treatment of the retina is large—for example, 1,000 to 1,500 spots are commonly burned. It may thus be readily appreciated that if the laser probe was a multi-spot probe enabling the burning of multiple spots at a time, the photocoagulation procedure would be faster (assuming the laser source power is sufficient). Accordingly, multi-spot laser probes have been developed and can be classified into two categories. A first category, denoted herein as a "multi-spot/multi-fiber" laser probe, produces its multiple laser beams through a corresponding array of optical fibers. A second category uses only a single fiber and is thus denoted herein as a "multi-spot/single-fiber" laser probe. Regardless of whether a laser probe is a single-fiber or multi-fiber probe, it should be compatible with the adapter used to connect the probes to the laser source. In that regard, it is conventional for a laser source to have a standardized interconnect such as a subminiature version A (SMA) interconnect. For example, the laser source may have a female SMA connector that receives a male SMA connector coupled to whatever instrument the laser source is driving. For a conventional single-spot/single-fiber laser probe, its male SMA connector will incorporate a single fiber. The laser source provides a focused beam known as the laser beam waist to the male SMA connector. This is quite advantageous for the single fiber probe since its optical fiber has its end face illuminated by the waist to enable efficient coupling to the laser source. But if a multi-spot/multi-fiber laser probe uses a corresponding plurality of fibers to drive its multiple spots, it cannot simply have its multiple fibers receive the focused beam from the source in this convenient single-fiber fashion because the laser waist is too narrow to couple into multiple fibers. Instead, the laser source would have to have its conventional interconnect changed or adapted so that the multiple fibers from the probe are not simply presented with the laser waist. But such changes are expensive and cumbersome.

Thus, a multi-spot/multi fiber probe has been developed such that the laser source drives a single fiber interconnect connected to a single fiber cable that in turn drives a single-fiber/multiple-fiber optical coupling within the laser probe handpiece. The resulting optics within the handpiece increase costs because it is desirable that the laser probe be disposable to limit contamination from patient to patient. For example, the optics include a diffractive beam splitter to split the beam from the single fiber into multiple beams for distribution to the multiple fibers. To collimate the laser beam from the single fiber onto the beam splitter and then condense the resulting multiple beams onto the multiple fibers requires plano-convex lenses. But it is very difficult to move such lenses to the laser source interconnect such that the remainder of the probe can be less expensive because of the relatively small inner diameter of such interconnects.

Another issue arises in multi-spot/multi-fiber laser probes in that the telecentric laser beams transmitted from the distal ends of the multiple fibers should be directed into different angular directions so as to properly distribute the resulting laser beam spots on the retina. To provide such distribution, a multi-spot/multi-fiber laser probe has been developed with the distal ends of the fibers bent into the desired angular directions. But such bending is cumbersome and increases costs as well.

To avoid the issues associated with the use of multiple fibers, the light beam from a single-fiber laser probe can be directed onto a diffractive beam splitter that splits the beam into multiple diffracted beams for transmission to the retina. However, the diffractive beam splitter must then focus the resulting diffracted beams, which requires the grating prescription to be spatially varying across the element. Not only does such a complication increase costs, the resulting spatially-varying diffractive beam splitter will reduce the overall performance. Such a design also makes varying the distance between the distal fiber end the diffractive element difficult.

Accordingly, there is a need in the art for improved multi-spot laser probes.

SUMMARY

In accordance with a first aspect of the disclosure, a multi-spot/multi-fiber laser probe is provided that includes a first adapter, the first adapter being operable to connect with an opposing second adapter on a laser source; a first GRIN lens within the first adapter, the first GRIN lens configured to receive a laser beam from the laser source at a proximal end of the first GRIN lens and to relay the received laser beam towards a distal end of the GRIN lens; and an array of optical fibers having a proximal end configured to receive the relayed laser light.

In accordance with a second aspect of the disclosure, a multi-spot/single-fiber laser probe is provided that includes a cannula; an optical fiber positioned within the cannula; a diffractive beam splitter within the cannula; and a GRIN lens within the cannula and arranged between a distal end of the optical fiber and the diffractive beam splitter, wherein the diffractive beam splitter is configured to split a focused laser beam from the GRIN lens into multiple diffracted laser beams.

In accordance with a third aspect of the disclosure, a method of splitting a beam from a laser source into multiple laser beams for photocoagulation therapy is provided that includes focusing the laser beam propagated from the laser source through a GRIN lens onto a diffractive beam splitter, wherein the GRIN lens and the diffractive splitter are arranged sequentially within a laser probe cannula; and adjusting a gap between the GRIN lens and the diffractive splitter to adjust a focused spot size for resulting multiple diffractive beams from the diffractive splitter.

In accordance with a fourth aspect of the disclosure, a multi-spot/single-fiber laser probe is provided that includes a cannula; an array of optical fibers within the cannula; and a GRIN lens within the cannula and adjacent a distal end of the array, the GRIN lens configured to focus a plurality of laser beams from the array of optical fibers into focused laser spots on a retina.

In accordance with a fifth aspect of the disclosure, a multi-spot/multi-fiber laser probe is provided that includes a first adapter, the first adapter operable to connect with an opposing second adapter on a laser source; a first GRIN lens within the first adapter, the first GRIN lens configured to receive a laser beam from the laser source at a proximal end of the GRIN lens and to relay the received laser beam towards a distal end of the GRIN lens as a collimated wave front; a diffractive beam splitter within first adapter adjacent the distal end of the first GRIN lens, wherein the diffractive beam splitter is configured to receive the collimated wave front so as to provide multiple diffracted beams; and a second GRIN lens within the first adapter adjacent to a distal end of the diffractive beam splitter, wherein the second GRIN lens is operable to focus the diffracted beams onto a proximal end face of an array of optical fibers.

DETAILED DESCRIPTION

An improved multi-spot/multi-fiber laser probe is provided that is compatible with conventional laser source interconnects. In addition, an improved multi-spot/single fiber laser probe is provided that does not require a spatially-varying diffractive beam splitter and also allows for convenient physical movement of the single fiber relative to a GRIN lens to enable spot size adjustment. Each embodiment has its own unique advantages. For example, the improved multi-spot/single fiber laser probe allows the surgeon to adjust the laser burn spot size. In contrast, the improved multi-spot/multi-fiber laser probe will have an inherent alignment between the illumination provided by the aiming beam and the resulting laser spots. Because this alignment is quite advantageous in that the surgeon will confidently know that the spot produced by the aiming beam accurately represents where the resulting laser burn spot will be, the multi-spot/multi-fiber laser probe is discussed first;

Multi-Spot/Multi-Fiber Laser Probe

Figure 1:
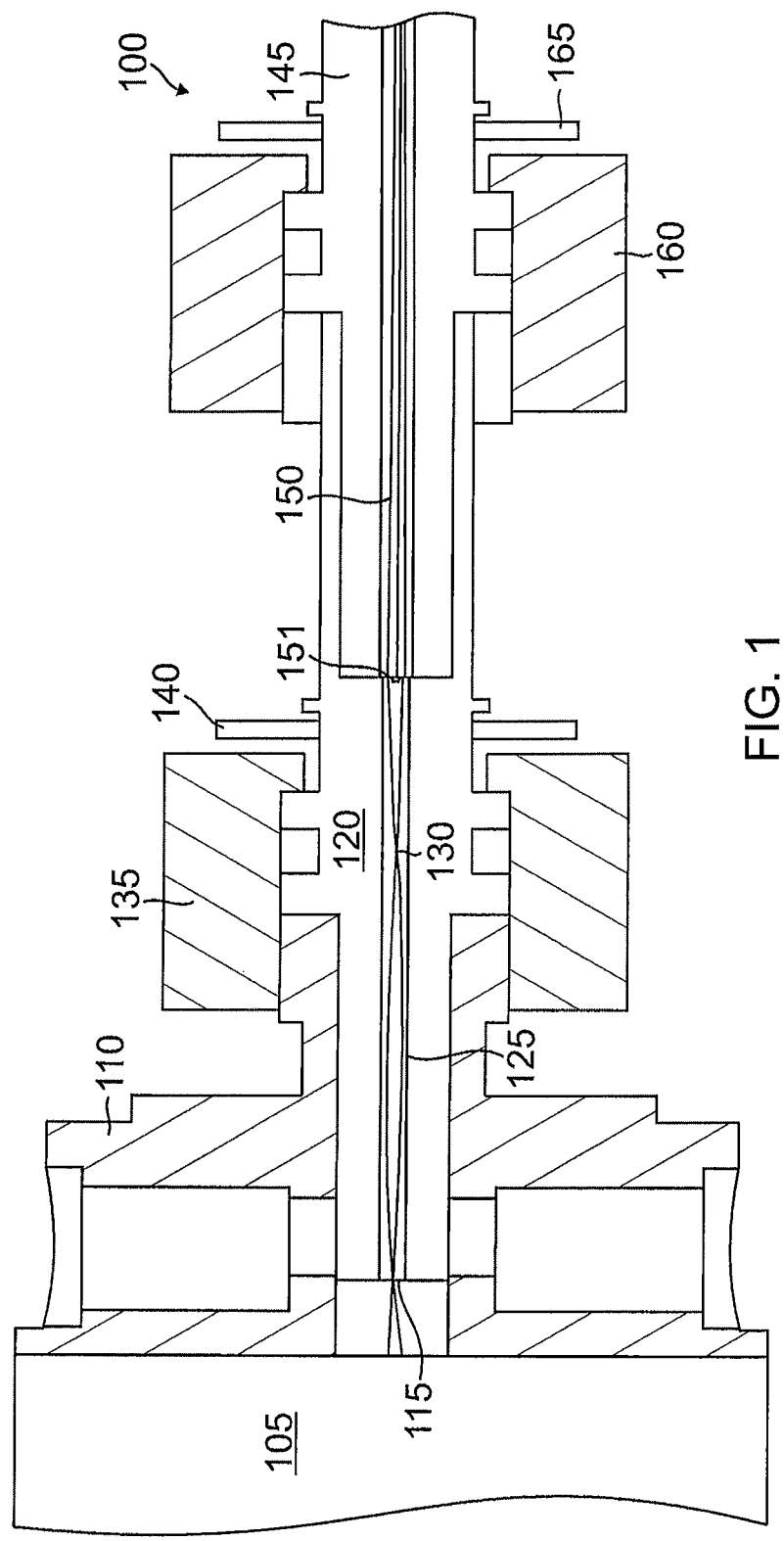
FIG. 1 is a longitudinal cross-sectional view of a laser source coupled to an adapter element containing a GRIN lens for coupling to a proximal end of a multi-spot/multi-fiber laser probe.

Turning now to the drawings, a multi-spot/multi-fiber laser probe 100 is shown in FIG. 1. As will be discussed further herein, laser probe 100 does not require any diffractive optics. A laser source 105 drives probe 100 through a suitable interconnect. A common standardized interconnect for laser source 105 is a subminiature version A (SMA) adapter. Thus, laser source 105 includes a female SMA adapter 110. However, it will be appreciated that laser probe 100 is readily adapted to mate with any conventional standardized optical interconnect so long as the laser source's interconnect presents a focused beam spot such as laser waist 115 to a proximal end of a male connector from the laser probe. Thus, the following discussion will assume that laser probe 100 couples to source 105 through a customized SMA adapter 120 without loss of generality.

To receive laser waist 115, the bore of SMA adapter 120 includes a gradient index (GRIN) lens 125. GRIN lens 125 may be a simple, single-element cylindrical GRIN rod lens that is readily inserted into such a bore. GRIN lens 125 is designed to relay the focused beam to a second focused spot 130 and then to a collimated beam wave front at its distal end. As known in the SMA arts, SMA adapter 120 secures to SMA adapter 110 through a threaded cylinder 135 and retaining ring 140. SMA adapter 120 has both a male end for insertion into SMA adapter 110 but also a female end that receives a conventional optical interconnect such a male SMA 905 fiber connector 145. Connecter 145 secures to adapter 120 through a threaded cylinder or ring 160 and retaining ring 165. Connector 145 includes in its bore an array of optical fibers 150. A proximal end 151 of array 150 is separated from the distal end of GRIN lens 125 by a suitable air gap such as a 220 μm air gap. Connector 145 connects to a flexible cable encasing fibers 150 that leads to a handpiece and cannula as known in the laser probe arts.

Figure 2:
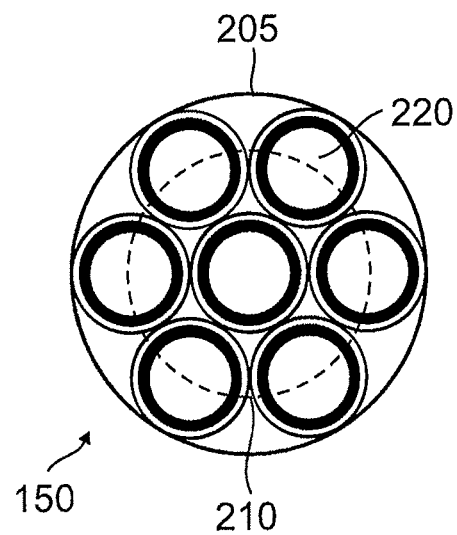
FIG. 2 shows a radial cross-sectional view of a multi-fiber array within the proximal end of the probe of FIG. 1.

An embodiment of fiber array 150 is shown in cross-section in FIG. 2. The laser beam boundary at the proximal end 151 of FIG. 1 is shown for both a green laser beam boundary 205 from source 105 as well as a red aiming beam boundary 210. Array 150 includes a central fiber circumferentially surrounded by six outer fibers. In one embodiment, each fiber 220 has a numerical aperture (NA) of 0.22 achieved through a 75 μm glass core encased in a 90 μm cladding surrounded by a 101 μm jacket. To minimize the amount of uncoupled laser energy into array 150, GRIN lens 125 is configured such that laser beam boundary 205 just encompasses the six outer fibers. The clocking of array 150 relative to the laser beam is not an issue as the laser beam and array 150 are axisymmetric. Array 150 extends to a distal end of the laser probe as discussed analogously with regard to FIG. 5.

One can immediately appreciate the advantageous properties of such a proximal interconnection in that no complicated, multi-lens relay system is required. Instead, GRIN lens 125 is readily inserted into the bore of adapter 120 that enables a standardized adapter such as male SMA adapter 145 to attach a disposable laser probe receiving fiber array 150. Without GRIN lens 125 and its adapter 120, standardized adapter 110 on laser source 105 would have to be changed, which is plainly undesirable since other attachments for source 105 would have to change in concert. Alternatively, the source's adapter could be left standardized but then a multi-lens relay system would be required. However, SMA adapter 120 and GRIN lens 125 eliminate such complications. Although SMA adapter 120 is thus quite advantageous, one can appreciate that roughly 50% of the laser energy is delivered to the interstices between the fibers in array 150 as seen in FIG. 2. This laser energy is thus unavailable for use in photocoagulation, thereby increasing the necessary laser source power and/or the amount of time necessary to produce the laser burn spots.

Figure 3:
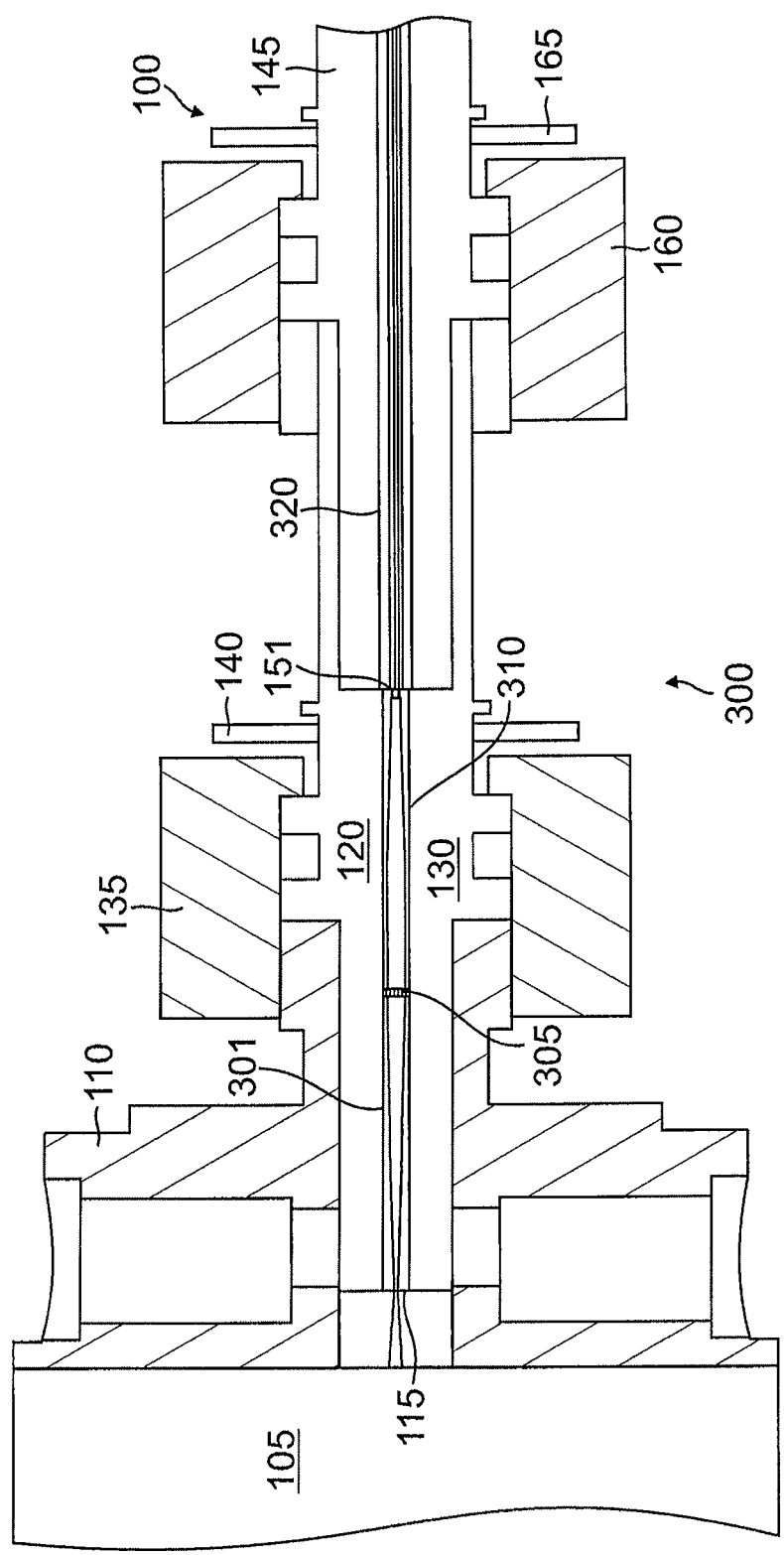
FIG. 3 is a longitudinal cross-sectional view of a laser source coupled to an adapter element including a diffractive beam splitter for coupling to a proximal end of a multi-spot/multi-fiber laser probe.

Turning now to FIG. 3, a diffractive embodiment that does not illuminate fiber array interstices is illustrated. As discussed with regard to FIG. 1, customized SMA adapter 120 permits a user to conveniently attach a disposable probe to adapter 120 to drive laser energy onto a fiber array. However, adapter 120 includes in its bore a diffractive beam splitter 305 arranged between a first GRIN lens 301 and a second GRIN lens 310.

Figure 4:
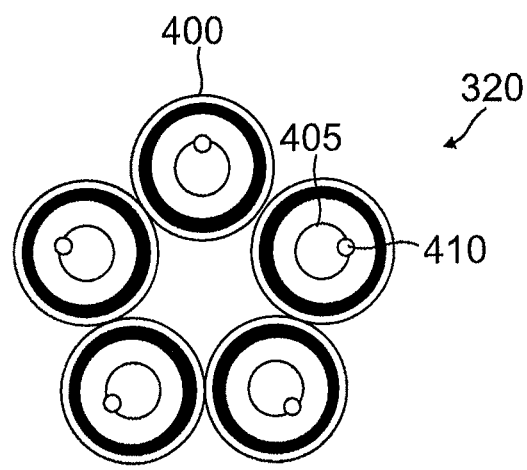
FIG. 4 is a radial cross-sectional view of a multi-fiber array within the proximal end of the probe of FIG. 3.

GRIN lens 301 is configured to collimate the laser beam diverging from laser waist 115 into a collimated wave front presented to diffractive beam splitter 305. GRIN lens 310 is configured to focus the resulting diffracted multiple laser beams from splitter 305 onto a proximal face 151 of a fiber array 320 contained within the bore of male SMA adapter 145. Fiber array 320 includes a plurality of fibers arranged according to the diffractive properties of diffractive beam splitter 305. For example, if diffractive beam splitter produces a symmetric pentagonal distribution of five diffracted beams, fiber array 320 is arranged in a corresponding pentagonal distribution. FIG. 4 shows such an arrangement for fiber bundle 320 at its proximal face 151.

In one embodiment, each optical fiber 400 has a 75 μm glass core clad in a 90 μm cladding that in turn is surrounded by a 101 μm jacket to achieve an NA of 0.22. The resulting projection of the diffracted green laser beams from splitter 305 is indicated by a boundary 405. Because diffraction is wavelength dependent, the projection of the aiming beam will have a different alignment with fiber array 320. Thus, splitter 305 and fiber array 320 are arranged such that boundary 405 is axially aligned with each fiber 400 whereas a boundary 410 of a red aiming beam is radially displaced with regard to a center or axis of each fiber.

In one embodiment, the off-axis displacement provided by splitter 305 to each green diffracted beam is 1.45 degrees. GRIN lens 310 focuses the resulting collimated and diffracted beams onto the entrance face of each fiber 400 in array 320. By such an appropriate clocking of array 320 relative to the diffracted beams, efficient coupling of the respective diffracted beam and the aiming beam into each fiber 400 is achieved. In that regard, other types of adapters such as a ferrule connector (FC) or a standard connector (SC) commonly used in the telecommunications industry may be used instead of SMA adapter 120 to assist in optimal clocking. As discussed with regard to FIG. 1, assembly of the optical components into SMA adapter 120 is advantageously convenient in that GRIN lenses 301 and 310 as well as intervening diffractive beam splitter 305 may have optical adhesive applied and then slid into the bore of adapter 120 and abutted end-to-end with each other. In contrast, an alignment of refractive lenses would be cumbersome and difficult in comparison.

With the laser beam from the source split and telecentrically propagated through the fiber array as discussed above with regard to either FIG. 1 or FIG. 3, there remains the issue of angularly projecting focused laser spots from the laser probe. A GRIN lens solution is disclosed in FIG. 5 with regard to fiber array 320 of FIG. 3, but it will be appreciated that an analogous embodiment is readily constructed for fiber array 150 of FIG. 1.

Figure 5:
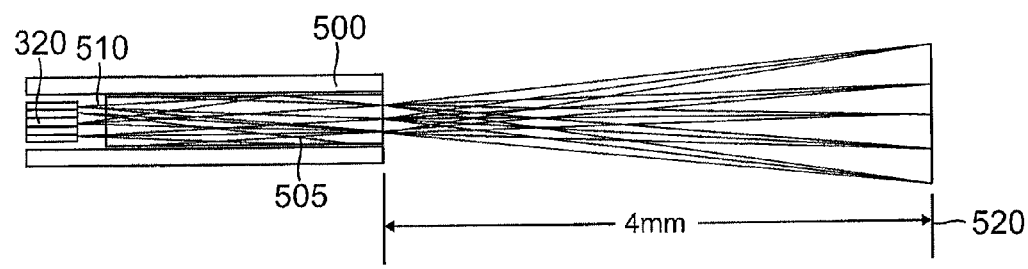
FIG. 5 illustrates a GRIN lens for angularly separating the projected multiple beams emitted from the multi-fiber array of FIG. 4.

As seen in FIG. 5, a laser probe cannula 500, e.g., a stainless steel cannula, receives a GRIN lens 505 at its distal end. A distal end of fiber array 320 is displaced within the cannula so as to project diverging beams 510 at a proximal end face of GRIN lens 505. GRIN lens 505 then focuses the beams on the retinal surface 520. The distribution of the resulting focused beams on the retina depends on the distribution of the fibers at the distal end of array 320.

In that regard, whereas the distribution at the proximal end of array 320 (FIG. 3) should be axially symmetric, one can arrange the fibers in any suitable distribution at the distal end. For example, as seen in FIG. 5, array 320 is linearly arranged at the distal end. The resulting laser spots are thus an enlarged version of the image (in this embodiment, a linear array) presented to GRIN lens 505. In one embodiment, GRIN lens 505 focuses the angularly-distributed beams at a distance of 4 mm from the distal end of cannula 500. Advantageously, GRIN lens 505 obviates any need for: bending the fibers into the desired angular distribution (and the associated problems of such bending), beveling the distal end faces of the fibers, or adding optical elements to the distal end faces. The fibers can even be touching one another in array 320 and GRIN lens 505 will still be effective. Multi-spot/single-fiber laser probe embodiments will now be discussed Multi-Spot/Single-Fiber Laser Probes Since a single fiber will carry a single laser beam, a diffractive beam splitter is provided to produce the necessary multiple laser beams to achieve simultaneous multiple laser burn spots. To avoid the need to build optical power into the diffractive beam splitter, a laser probe 600 of FIG. 6 includes a collimating GRIN lens 605 whose proximal end abuts a distal end of a single glass fiber 610 within a cannula 615 for probe 600. A centering cylinder 620 circumferentially surrounds fiber 610 to keep the fiber centered within the cannula. GRIN lens 605 presents a collimated laser beam wave front to a diffractive beam splitter 630. In one embodiment, splitter 630 is configured to produce 5 diffracted and collimated beams at an angular separation of 11 degrees that are focused at a distance of 4 mm from a distal end of cannula 615 as discussed analogously with regard to FIG. 3. The assembly of probe 600 is advantageously convenient in that fiber 610 and its centering cylinder 620 are distally retracted within the cannula. GRIN lens 605, having optical adhesive applied to its outer surfaces, is then pushed into the cannula bore until it abuts a distal end of fiber 610 and cylinder 620, followed by an insertion of splitter 630, which also has optical adhesive on its side walls. The fiber 610 and cylinder 620 may then be distally displaced within the cannula bore to align a distal end of splitter 630 with the distal end of cannula 615, whereupon the adhesive is allowed to set. Moreover, index-matching adhesive may be used at the junction of fiber 610 and GRIN lens 605 as well as between lens 605 and splitter 630 to eliminate any Fresnel reflection losses.

Figure 6:
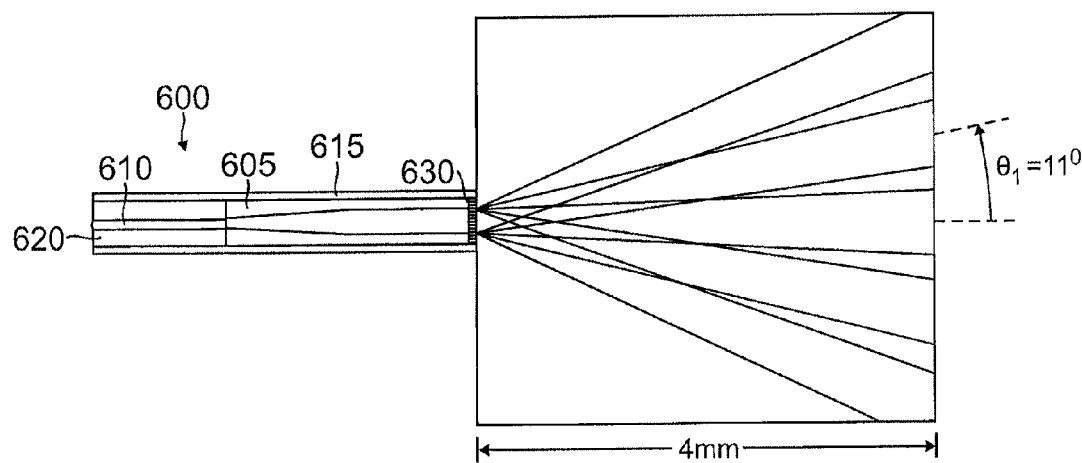
FIG. 6 is a longitudinal cross-sectional view of the distal end of a multi-spot/single-fiber laser probe cannula that incorporates a diffractive beam splitter.
Figure 7:
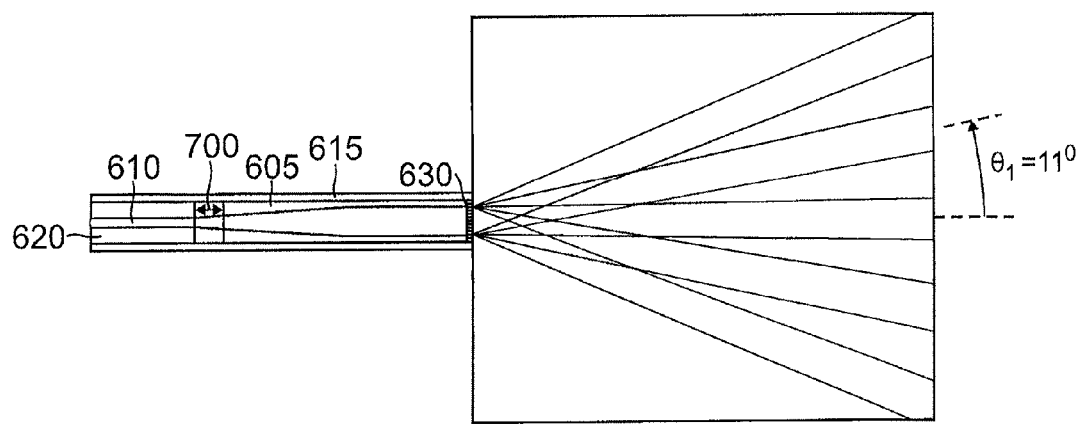
FIG. 7 is a longitudinal cross-sectional view of the distal end of the multi-spot/single-fiber laser probe cannula of FIG. 6 modified with an air gap between the diffractive beam splitter and the single fiber the resulting multiple laser beams to focus on the retina.

FIG. 7 shows an alternative embodiment in which the separation between the distal end of fiber 610 and GRIN lens 605 is left unfixed. In this fashion, by actuating a mechanical coupling (not illustrated) to fiber 610 and it cylinder 620, a surgeon may adjust the size of a gap 700 between fiber 610 and lens 605. With no gap such as illustrated in FIG. 6, the diffracted beams are collimated. However, by introducing gap 700, the diffracted beams are converging rather than collimated, which produces smaller focused laser spots on the retina. Thus, by distally or proximally displacing the mechanical coupling, a surgeon can adjust the laser beam spot size on the retina in real time responsive to therapeutic goals. Although such adjustment has its advantages, it can be observed that the diffractive beam splitter 605 will necessarily diffract a red aiming beam into different angular directions than the degrees of separation illustrated in FIGS. 6 and 7 for green laser light. This wavelength-dependent displacement is analogous to the displacement seen in FIG. 4 with regard to the red and green laser spot boundaries on the individual fiber end faces. Such displacement is rather undesirable since the point of the aiming beam is to indicate where the corresponding laser burn spot is produced. In contrast, the multi-spot/multi-fiber embodiments discussed with regard to FIGS. 1 and 3 will not have such displacement between the aiming beam spots and the laser beam spots.

Embodiments described above illustrate but do not limit the invention. It should also be understood that numerous modifications and variations are possible in accordance with the principles of the present invention. Accordingly, the scope of the invention is defined only by the following claims.

I claim:

1. A multi-spot/multi-fiber laser probe, comprising:
   a first adapter, the first adapter operable to connect with an opposing second adapter on a laser source;
   a first GRIN lens within the first adapter, the first GRIN lens configured to receive a laser beam from the laser source at a proximal end of the GRIN lens and to relay the received laser beam towards a distal end of the GRIN lens as a collimated wavefront, the first GRIN lens being disposed within the first adapter in a position to receive the laser beam at a first focused beam spot from the laser source when the first adaptor is connected with the second adapter;
   a diffractive beam splitter within first adapter adjacent the distal end of the first GRIN lens, wherein the diffractive beam splitter is configured to receive the collimated wavefront so as to provide multiple diffracted beams;
   a second GRIN lens within the first adapter adjacent to a distal end of the diffractive beam splitter, and
   an array of optical fibers, wherein the second GRIN lens is operable to focus the diffracted beams onto a proximal end face of the array.

2. The multi-spot/multi-fiber laser probe of claim 1, wherein each focused diffracted beam from the second GRIN lens is substantially centered on a respective one of the optical fibers in the array.

3. The multi-spot/multi-fiber laser probe of claim 1, wherein the first adapter is operable to connect with a third adapter, and wherein the array of optical fibers is within the third adapter.

4. The multi-spot/multi-fiber laser probe of claim 3, wherein the first, second, and third adapters are SMA adapters.

* * * * *